United States Patent [19]

Ottow et al.

[11] Patent Number: 4,829,060
[45] Date of Patent: May 9, 1989

[54] 11 BETA-N,N-DIMETHYLAMINOPHENYL-ESTRADIENES, THEIR MANUFACTURE AND PHARMACEUTICAL PREPARATIONS CONTAINING THEM

[75] Inventors: Eckhard Ottow; Guenter Neef; Ralph Rohde; Rudolf Wiechert; Sybille Beier; Walter Elger; David Henderson, all of Berlin, Fed. Rep. of Germany

[73] Assignee: Schering Aktiengesellschaft, Berlin and Bergkamen, Fed. Rep. of Germany

[21] Appl. No.: 832,604

[22] Filed: Feb. 24, 1986

[30] Foreign Application Priority Data

Feb. 22, 1985 [DE] Fed. Rep. of Germany ....... 3506785

[51] Int. Cl.$^4$ .......................... A61K 31/56; C07J 1/00
[52] U.S. Cl. .................... 514/179; 514/182; 260/397.45; 260/397.47; 260/397.5
[58] Field of Search .......... 260/397.45, 397.5, 397.47; 514/179, 182

[56] References Cited

U.S. PATENT DOCUMENTS

| 4,447,424 | 5/1984 | Teutsch et al. | 260/397.45 |
| 4,519,946 | 5/1985 | Teutsch et al. | 260/397.1 |
| 4,536,401 | 8/1985 | Neef et al. | 514/173 |

FOREIGN PATENT DOCUMENTS 0129499 12/1984 European Pat. Off. .
3347126 7/1985 Fed. Rep. of Germany .

OTHER PUBLICATIONS

Chemical Abstracts, vol. 104 (1986) #186715e; Rohde et al.
Chemical Abstracts, vol. 103 (1985) #6617y; Neef et al.
Steroids; vol. 44, No. 4; Oct. 1984, pp. 349–372; Neef et al.
Chemical Abstracts; vol. 104 (1986) #34230F; Neef et al.

Primary Examiner—Leonard Schenkman
Assistant Examiner—Joseph A. Lipovsky
Attorney, Agent, or Firm—Millen & White

[57] ABSTRACT

Descriptions are given of 11β-aryl-estradienes of general formula I

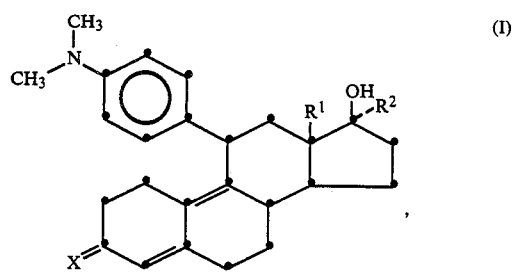

where
X means an oxygen atom or a hydroxyimino group N~OH, where the hydroxy group may be in the syn or anti position,
$R^1$ means a methyl or ethyl group
$R^2$ means a —C≡C—CH=CH$_2$, a —CH$_2$—(CH$_2$)$_n$—Y—R$^3$ or a —CH=CH—(CH$_2$)$_m$—Y—R$^3$ group,
Y standing for an oxygen or sulfur atom, n for numbers 0 or 1, m for numbers 1, 2 or 3 and R$^3$ for a hydrogen atom, for an alkyl or acyl radical with 1 to 4 carbon atoms respectively, with the proviso that when m stands for 1 and Y for an oxygen atom, R$^3$ means an alkyl radical with 1 to 4 carbon atoms.

The new 11β-aryl-estradienes possess antigestagenic and antiglucocorticoid effects.

30 Claims, 1 Drawing Sheet

11 BETA-N,N-DIMETHYLAMINOPHENYL-ESTRADIENES, THEIR MANUFACTURE AND PHARMACEUTICAL PREPARATIONS CONTAINING THEM

BACKGROUND OF THE INVENTION

This invention relates to new 11β-phenyl-estradienes, processes for their manufacture and pharmaceutical preparations containing them.

11β-phenyl estradienes are already known. Thus, for example 11β-aryl-17α-propinyl- and -ethynyl-4,9(10)estradienes are described in European Patent Application No. 82400025.1 (Publication No. 0 057 115) and U.S. patent specification Nos. 4,386,085 and 4,447,424 as well as 11β2 -phenyl-17α-(3-hydroxypropyl)-4,9(10)-estradienes in European Patent Application No. 84101721.3 (Publication No. 0 116 974 and U.S. Pat. No. 4,536,401). These compounds have a strong affinity for gestagen receptors without themselves possessing gestagenic activity. They are competitive antagonists of progesterone (antigestagens) and are suitable for inducing abortion since they displace from the receptor the progesterone required to maintain pregnancy. They are therefore valuable and interesting with regard to their use in post-coital fertility control.

They can also be used for treatment of hormonal irregularities, to induce menstruation and to induce birth.

The compounds set out in European Patent Application No. 84101721.3 also have anti-mineral-corticoid effects in addition to their antigestagenic properties.

On the other hand, the 11β-aryl-17α-propinyl- and -ethinyl-4,9(10)-estradienes first mentioned also display antiglucocorticoid activity and can thus be used as pharmaceuticals for therapy of corticoid-induced disorders (glaucoma) and to control side effects that occur during long-term treatment with glucocorticoids (Cushing's syndrome). They therefore also make it possible to control disorders due to a supersecretion of glucocorticoids, above all adipositas, arteriosclerosis, osteoporosis, diabetes and insomnia.

SUMMARY OF INVENTION

It is an object of this invention to provide new compounds having improved pharmacological properties.

Upon further study of the specification and appended claims, further objects and advantages of this invention will become apparent to those skilled in the art.

These objects have been achieved by providing 11β-aryl-estradienes of formula I where X is an oxygen atom or a hydroxyimino group N~OH, wherein the hydroxy group may be in the syn or anti position, $R^1$ is methyl or ethyl, $R^2$ is —C≡C—CH=CH$_2$, —CH$_2$—(CH$_2$)$_n$—Y—R$^3$ or —CH=CH—(CH$_2$)$_m$—Y—R$^3$, Y is oxygen or sulfur, n is a number 0 or 1, m is a number 1, 2 or 3 and $R^3$ is hydrogen or alkyl or acyl each of 1 to 4 carbon atoms, with the proviso that when m is 1 and Y is oxygen, $R^3$ is alkyl of 1 to 4 carbon atoms.

These objects have also been achieved by providing corresponding pharmacological compositions and methods of use as well as processes of preparing the compounds.

DETAILED DESCRIPTION

It has now been found that the new compounds of formula I display, suprisingly, much stronger effects than the known compounds of this class of substances. In this connection, either of the antigestagenic or the antiglucocorticoid effect can be stronger or both effects can be stronger, than in the compounds hitherto known.

The abortive effect was determined to distinguish the antigestagenic effect.

The experiments were performed on rats weighing approximately 200 g. After mating, the beginning of pregnancy was ascertained by demonstrating the presence of sperm in vaginal smears. The day on which the presence of sperm was verified is considered the first day of pregnancy (=d 1 p.c.)

After nidation of the blastocysts from d5 p.c. to d7 p.c., the animals were treated with the desired substance to be tested or the solvent. On d9 p.c., the animals were killed and the uteri examined for implants and places of resorption. Photographs were made of all the uteri. The absence of implants was classified as an abortion.

The test substances were dissolved in a mixture of benzyl benzoate and castor oil (ratio of 1:9). The vehicle volume for individual dose amounts to 0.2 ml. Treatment was subcutaneous (s.c.).

The superiority of the compounds in accordance with the invention was demonstrated by comparing the biological properties of a compound in accordance with the invention, 17β-(4-dimethylaminophenyl)-17α-(methoxymethyl)-17β-hydroxy-4,9-estradien-3-one (A), 11β-(4-dimethyl-aminophenyl)-17β-hydroxy-17α-(propin-1-yl)-4,9(10)-estradien-3-one, RU 38486, described in European Pat. No. 82400025.1 (B) and the 11β-(4-dimethylaminophenyl)-17β-hydroxy-17α-(3-hydroxypropyl)-4,9(10)-estradien-3-one in EP No. 84101721.3 (C).

TABLE 1

| | Abortion Test with Pregnant Rats | |
|---|---|---|
| Substance | Dose mg/animal/day s.c. | Abortion Rate n abortions positive/n total |
| A | 10.0 | 4/4 |
| | 3.0 | 3/3 |
| | 1.0 | 3/3 |
| B | 10.0 | 4/4 |
| | 3.0 | 4/4 |
| | 1.0 | 2/4 |
| C | 10.0 | 4/4 |
| | 3.0 | 4/4 |

TABLE 1-continued

Abortion Test with Pregnant Rats

| Substance | Dose mg/animal/day s.c. | Abortion Rate n abortions positive/n total |
|---|---|---|
| | 1.0 | 0/4 |

From Table 1 it can be seen that only compound A in accordance with the invention haa a fully abortive effect at a dose of 1 mg, i.e it is more effective than the state-of-the-art compounds by a factor of 3 (Endocrinoloy 1984, 239).

The influence on the tyrosine aminotransferase of the substances in accordance with the invention was ascertained to distinguish the antiglucocorticoid effect. The test system is based on measurement of the activity of the liver enzyme tyrosine aminotransferase (TAT) in cultures of RHC (rat hepatoma cells). The enzyme catalyzes the first step in the metabolism of tyrosine and can be induced by glucocorticoids in both the liver and hepatoma cells. The activity is easy to measure in crude extracts (Granner and Tomkins, (1970) Meth. Enzymol. 15, 633). The enzyme transfers the amino group of tyrosine to 2-oxo-glutaric acid. This results in glutaminic acid and p-hydroxyphenyl pyruvate. In an alkaline solution the more stable p-hydroxybenzaldehyde is formed from the p-hydroxyphenyl pyruvate, the absorption of the former being measured at 331 nm. Dose-dependent induction of the TAT activity in RHC cells is achieved with cortisol (max. activity at $10^{-6}M$) or dexamethasone (max. activity at $10^{-7}M$). It is possible to stimulate activity by a factor of 4 to 6 as compared with the basal value. Simultaneous treatment with corticoid and antiglucocorticoid leads to a decrease in TAT activity.

In this test, compound A in accordance with the invention displays the same activity as RU 38.486 (B), a substance that can be viewed as standard (7th International Congress of Endocrinology, July 1–7, 1984, Quebec City, Canada; Excerpta Medica, Amsterdam-Oxford-Princeton; Drugs of the Future 9, 755, 1984).

Another example in accordance with the invention that should be mentioned is 11β-(4-dimethylaminophenyl)-17α-(but-1-in-3-enyl)-17β-hydroxy-4,9-estradien-3-one (D); in the antigestagen test this compound displays an effect similar to that of RU 38.468 (B), and in the TAT test for antiglucocorticoid effect it is stronger than RU 38.486 (B).

The antithymolysis test is an in-vivo test of the antiglucocorticoid effect in rats. It is based on the fact that glucocorticoids induce suppression of the thymus. Cancellation or reduction of this corticoid effect is to be expected from substances with an antiglucocorticoid effect. In this test male adrenalectomized rats are injected for four days with the test substances in combination with an effective standard dose of dexamethasone amounting to 0.01 mg/d s.c. The autopsy is performed on the 5th day. The weight of the thymus is then determined. To assess the antiglucocorticoid effect of the test substance the difference in thymus weights between the solvent control (benzyl benzoate/castor oil mixture in a ratio of 1:4) and the group receiving dexamethasone alone is specified as 100%. The average antiglucocorticoid effect in percent is calculated (=cancellation in % of thymus suppression induced by dexamethasone).

Figure 1A:
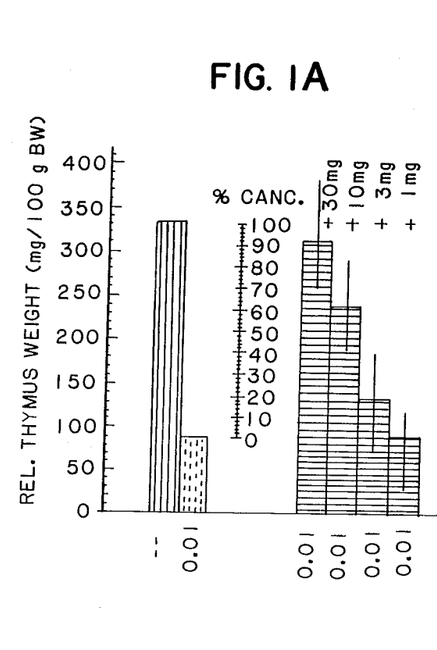
FIGS. 1A and 1B demonstrate the influence of 11β-(4-dimethylaminophenyl)-17α-(methoxymethyl)-17β-hydroxy-4,9-estradien-3-one (A) on thymus suppression induced by dexamethasone. Specifically, the figures detail treatment of adrenalectomized male rats weighing 100-130 g for 4 days (dose in mg/d s.c.); determination of thymus weight was made on the fifth day. (n=6 animals/group; 95% confidence interval for % cancellation.)
Figure 1B:
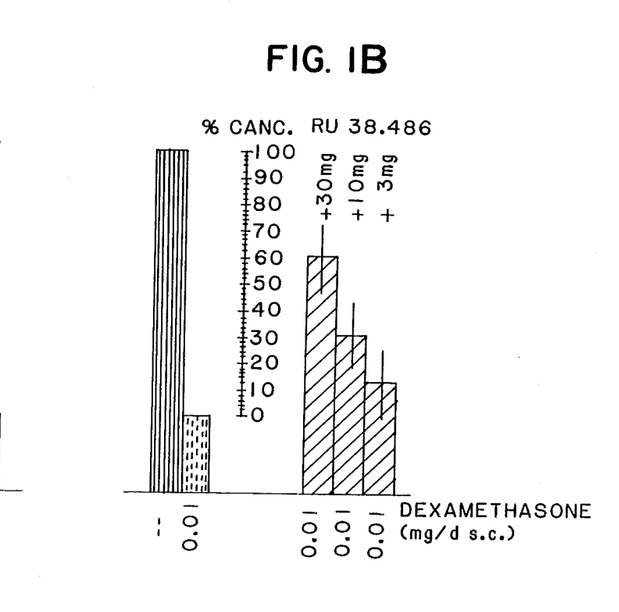

As FIGS. 1A and 1B and Table 2 show, compound A in accordance with the invention and mentioned by way of example has a much stronger antiglucocorticoid effect in the in-vivo antithymolysis test than compound RU 38.486 (B) which is viewed as a standard.

TABLE 2

Cancellation of thymus suppression induced by dexamethasone

| Treatment | | Rel. thymus weight (mg/100 g body weight) average | Cancellation of corticoid effect in % |
|---|---|---|---|
| Dexamethasone (mg/d s.c.) | Substance (mg/d s.c.) | | |
| — | — | 331.0 | |
| 0.01 | — | 86.7 | |
| 0.01 | 3.0 | 130.6 | 18.0 |
| 0.01 | A 10.0 | 235.5 | 60.9 |
| 0.01 | 30.0 | 309.0 | 91.0 |
| — | — | 385.4 | |
| 0.01 | — | 87.2 | |
| 0.01 | 3.0 | 125.6 | 12.9 |
| 0.01 | B 10.0 | 178.1 | 30.5 |
| 0.01 | 30.0 | 264.7 | 59.5 |

In Formula I, suitable alkyl groups include methyl, ethyl, n- and i- propyl, and n-, sec-, iso- and t-butyl. Suitable alkanoyl groups include alkanoyl groups based on the same alkyl groups. Preferred groups are methyl, ethyl, formyl, acetyl and propionyl.

The invention also relates to pharmaceutical preparations containing compounds of general formula I useful, e.g., to treat mammals including humans. The pharmacologically effective compunds of general formula I in accordance with the invention can be processed by the generally known galenical methods into pharmaceutical preparations for enteral, percutaneous or parenteral application.

Conventional excipients are pharmaceutically acceptable organic or inorganic carrier substances suitable for parenteral, enteral or topical application which do not deleteriously react with the active compounds. Suitable pharmaceutically acceptable carriers include but are not limited to water, salt solutions, alcohols, gum arabic, vegetable oils, polyethylene glycols, gelatine, lactose, amylose, magnesium stearate, talc, silicic acid, viscous paraffin, perfume oil, fatty acid monoglycerides and diglycerides, pentaerythritol fatty acid esters, hydroxymethylcellulose, polyvinyl pyrrolidone, etc. The pharmaceutical preparations can be sterilized and if desired mixed with auxiliary agents, e.g., lubricants, preservatives, stabilizers, wetting agents, emulsifiers, salts for influencing osmotic pressure, buffers, coloring, flavoring and/or aromatic substances and the like which do not deleteriously react with the active compounds.

For parenteral application, particularly suitable are injectable sterile solutions, preferably oily or aqueous solutions, as well as suspensions, emulsions, or implants, including suppositories. Ampoules are convenient unit dosages.

For enteral application, particularly suitable are tablets, dragees, suppositories or capsules having talc and/or a carbohydrate carrier or binder or the like, the carrier preferably being lactose and/or corn starch and/or potato starch. A syrup, elixir or the like can be used wherein a sweetened vehicle is employed. Sustained release compositions can be formulated including those wherein the active compound is protected with differentially degradable coatings, e.g., by microencapsulation, multiple coatings, etc.

Generally, the compounds of this invention are dispensed in unit dosage form comprising 10–100 mg in a pharmaceutically acceptable carrier per unit dosage. The dosage of the antigestagenic compounds according to this invention generally is about 1-1,000 mg/day when administered to patients, e.g., humans preferably 5-200 mg/day to induce abortions or trigger menstruation analogous to the known agent RU 486. The dosage of the compounds of this invention generally is 1-500 mg/day when administered to such patients, preferably 1-100 mg/day, to treat, e.g., Cushing Syndrome. Suitable dosage and regimens for a given host can be determined using conventional considerations, e.g., by customary comparison of the differential activities of the subject compound and of a known agent, e.g., by means of an appropriate, conventional pharmacological protocol.

The new 13-alkyl-11β-phenylestradienes of general formula I can be prepared in accordance with this invention by a method wherein a compound of general formula II wherein K represents a blocked ketone group in the form of the ketal, thioketal, oxime or methyloxime, $R^1$ is as defined above and $R^{2'}$ has one of the meanings for $R^2$, any hydroxy or mercapto groups being conventionally protected, is subjected to the influence of a dehydrating agent, which is also capable of releasing the protected function, thereby separating water while simultaneously forming the 4(5) double bond, and, optionally, a hydroxy or mercapto group present in $R^2$ is etherified or esterified, thereby forming the product of general formula I wherein X is an oxygen atom and, optionally, a resultant compound is reacted with hydroxylamine hydrochloride in the presence of tertiary amines at temperatures of between $-20°$ C. and $+40°$ C. to form compounds wherein X is N~OH.

The starting compounds of general formula II are treated with acid or an acid ion exchanger to split off water while forming the 4(5) double bond and simultaneously to remove any protected groups. The acid treatment is performed in the way known in the art, e.g., the compound of formula II, which contains at least one protected group, is dissolved in a solvent mixable with water, like aqueous methanol, ethanol or acetone, and the solution is allowed to react with catalytic amounts of mineral or sulfonic acid, like hydrochloric acid, sulfuric acid, phosphoric acid, perchloric acid or p-toluene sulfonic acid, or an organic acid, like acetic acid, until the water has split off and the protected group(s) is (are) removed. The reaction, which takes place at temperatures of 0° to 100° C., can also be undertaken with an acid ion exchanger. The course of the reaction can be followed by analytical methods, for example by thin-layer chromatography of samples.

In an acid milieu, the protected groups K or those in $R^{2'}$ in general formula II are easily splittable groups, for example, the ethylenedioxyketal, ethylenedithioketal, 2,2-dimethyltrimethylenedioxyketal, hydroxyimino, methoxyimino, tetrahydropyranyl, methoxymethyl or ethoxymethyl group.

If desired, the compounds of general formula I wherein X is an oxygen atom can be converted by reaction with hydroxylamine hydrochloride in the presence of tertiary amines at a temperature of between $-20°$ and $+40°$ C. into oximes (formula I, with X in the meaning of the hydroxyimino grouping N~OH, where the hydroxy group may be in the syn or anti position). Suitable tertiary bases include, for example, trimethylamine, triethylamine, pyridine, N,N-dimethylaminopyridine, 1,5-diazabicyclo [4.3.0]nonene-5 (DBN) and 1,5-diazabicyclo[5.4.0]undecene-5 (DBU), pyridine being preferred.

If esterification or etherification of the compounds of general formula I is desired on its substituent $R^2$ containing a hydroxy or mercapto group, this acylation or etherification is done in a manner known in the art. Esterification is accomplished, for example, by converting with acid anhydride into pyridine at room temperature. Etherification can be performed, for example, with methyl iodide in the presence of a base, e.g., n-butyllithium.

The manufacture of the starting compounds of general formula II starts, as described for example in European patent application Nos. 84101721.3 and 82400025.1, with the known epoxide of general formula III The 11-phenyl radical is introduced, with formation of the $\Delta^{9,10}$-5α-hydroxy structural element, either by means of a Grignard reaction catalyzed with Cu(I), with the corresponding aryl magnesium halogenides (Tetrahedron Letters 1979, 2051), or by reaction with the mixed organocuprates of the type $R_2Cu(CN)Li_2$ (J Amer. Chem. Soc. 103 (1981) 7672).

The $R^2$ substituents are introduced in accordance with the customary methods of building a $C_{17}$ side chain by nucleophilic addition to the 17-ketone, or to the 17-spirooxirane of the corresponding general formula IV producible therefrom

[M. Huebner et al, Journal f. prakt. Chemie 314, 667 (1972), M. Huebner et al, DOS No. 23 35 143 (1973), Arnzneim. Forsch. 30, 401 (1980)] wherein K is as defined above and, as is well-known, where necessary, by subsequent reactions (e.g., see "Terpenoids and Steroids", Specialist Periodical Report, The Chemical Society, London, Vol. 1-12).

For example, the spirooxirane can be opened to the corresponding 17β-substituted derivatives in a manner known in the art (cf. e.g. K. Ponsold et al, W.P. GDR 2259 [1968], K. Ponsold et al, Z. Chem. 11, 106 [1971]), e.g. by reaction with sodium methylate (to the 17α-ethoxymethyl compound) or, for example, with sodium thioethylate (to the 17α-ethylthiomethyl compound).

The but-1-in-3-enyl side-chain can be introduced into the 17α-position by allowing the 17-ketone to react with butin-yl-THP-ether in the presence of a base, e.g. potassium-t-butylate, with simultaneous splitting off of 2-hydroxy-tetrahydropyrane.

3-hydroxypropine,-propene or -propane are introduced into position 17 by converting the 17-ketone with the metallized derivatives of the propargyl alcohol, e.g. with 1-lithium-3-tetrahydropyran-2'-yloxy-propine-1, into the 17-(3-hydroxy-1-propinyl)-17-hydroxy compounds, which can subsequently be hydrogenated into the 17-(3-hydroxypropyl or 3-hydroxy-propenyl)-17-hydroxy compounds. The hydrogenation must take place in conditions that ensure exclusively an attack on the threefold C—C bond without saturating any existing tetra-substituted 9(10) double bond. This is achieved, for example, by hydrating at room temperature and normal pressure in solvents like methanol, ethanol, propanol, tetrahydrofurane (THF) or acetic ether with the addition of noble-metal catalysts like platinum or palladium.

The homologous hydroxyalkine, hydroxyalkene and hydroxyalkane groups are introduced in corresponding fashion with homologues of the propargyl alcohol.

The compound with the Z-configurated double bond in the hydroxypropenyl group results from hydrogenation of the acetylenic triple bond with a deactivated noble-metal catalyst (J. Fried, J. A. Edwards: Organic Reactions in Steroid Chemistry, Van Nostrand Reinhold Company 1972, p. 134, and H. O. House: Modern Synthetic Reactions 1972, p. 19). Suitable deactivated noble-metal catalysts are, for example, 10% palladium on barium sulfate in the presence of an amine or 5% palladium or calcium carbonate with the addition of lead(II)-acetate. The hydrogenation is stopped after one equivalent of hydrogen is taken up.

The compound with the E-configurated double bond in the hydroxypropenyl group results from reduction of the acetylenic triple bond in the generally known way. The literature describes a whole number of methods for converting alkines into transolefins, for example reduction with sodium in liquid ammonia (J. Am. Chem. Soc. 63 (1941) 216), with sodium amide in liquid ammonia (J. Chem. Soc. 1955, 3558), with lithium in low-molecular weight amines (J. Am. Chem. Soc. 77 (1955) 3378), with boranes (J. Am. Chem. Soc. 93 (1971) 3395 and 94 (1972) 6560), with diisobutyl aluminum hydride and methyllithium (J. Am. Chem. Soc. 89 (1967) 5085) and especially with lithium aluminum hydride/alcoholate (J. Am. Chem. Soc. 89 (1967) 4245). Another possibility is reduction of the triple bond with chromium(II)-sulfate in the presence of water or dimethylformamide in a weakly acid milieu (J. Am. Chem. Soc. 86 (1964) 4358) as well as, in general, reduction by reaction of transition-metal compounds with a change in the oxidation state.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever. In the preceding text and the following examples, all temperatures are set forth uncorrected in degrees Celsius and all parts and percentages are by weight, unless otherwise indicated.

EXAMPLE 1

11β-(methylaminophenyl)-17α-(but-1-in-3-enyl)-17β-hydroxy-4,9(10)-estradien-3-one 1.1 g of 11β-(4-dimethylaminophenyl)-17α-(but-1-in-3-enyl)-3,3-(2,2-dimethylpropane-1,3-dioxy)-9(10)-estrene-5α-17β-diol are stirred in 7 ml of 70% acetic acid for one hour at 45° C. The aqueous phase is subsequently neutralized with a saturated solution of NaHCO$_3$ and extracted with methylene chloride. Drying of the combined organic phases over Na$_2$SO$_4$, removal of the solvent in a vacuum and chromatography of the residue on silica gel with hexane/acetic ether yield 633 mg (71%) of the title compound.

| IR (KBr): | 3440 | cm$^{-1}$ | OH |
|---|---|---|---|
| | 1655 | } | unsaturated ketone |
| | 1615 | | |
| | 1520 | | aromatic substance |

$^1$H—NMR (TMS as internal standard; CHCl$_3$):
δ (ppm)  0.58 (3H,s,H-18); 2.92 ((H,s,N(CH$_3$)$_2$);
4.25-4.45 (1H,m,H-11);
5.35-6.05 (3H,m-H-olefin.); 5.75 (1H,s,H-4);
6.85 (4H,dd,J$_1$=9 and J$_2$=33 Hz, H-aromat.).

The starting material is prepared in the following way:

1.64 ml (10 mmoles) of butinyl-THP-ether and 2.24 g (20 mmoles) of potassium tert. butylate are added at room temperature to a solution of 987 mg (2 mmoles) of 11β-(4-dimethylaminophenyl)-3,3-(2,2-dimethylpropane-1,3-dioxy)-5α-hydroxy-9(10)-estren-17-one in 20 ml of abs. tetrahydrofurane (THF). After three hours of stirring the reaction mixture is poured into a mixture of 10 ml of 2N HCl and 40 ml of saturated NH$_4$Cl solution, and the aqueous phase is extracted with methylene chloride. The combined organic phases are dried over Na$_2$SO$_4$ and concentrated in a vacuum. Chromatography on aluminum oxide (stage III, neutral) with hexane/acetic ether yields 1.191 g (92%) of the desired product.

EXAMPLE 2

11β-(4-dimethylaminophenyl)-17α-(methoxymethyl)-17β-hydroxy-4,9(10)-estradien-3-one 1.024 g (1.9 mmoles) 11β-(4-dimethylaminophenyl)-17α-(methoxymethyl)-3,3-(2,2-dimethylpropane-1,3-dioxy)-9(10)-estrene-5α,17β-diol are converted as described in Example 1. This yields 900 mg of the crude product. Chromatography over silica gel with hexane/acetic ether yields 669 mg (78%) of the desired final compound.

$[\alpha]_D^{25} = 203.5°$ (c=1.03; CHCl$_3$).

The initial material is prepared in the following way:

(a)

11β-(4-dimethylaminophenyl)-5α-hydroxy-3,3-(2,2-dimethylpropane-1,3-dioxy)-9(10)-estrene-17β-spiro-1',2'-oxirane 2.6 g (5.3 mmoles) of 11β-(4-dimethylaminophenyl)-3,3-(2,2-dimethylpropane-1,3-dioxy)-5α-hydroxy-9(10)-estren-17-one are dissolved in 50 ml of abs. dimethylformamide under inert gas and successively mixed with 2.15 g of trimethylsulfonium iodide (10.6 mmoles) and 1.18 g (10.6 mmoles) of potassium tert.-butylate. After subsequent stirring for 16 hours at room temperature the reaction mixture is poured into 110 ml of saturated NaHCO$_3$ solution, the organic phase separated and the aqueous phase extracted with acetic ether. 2.67 g of the crude product are isolated after the combined organic phases are dried over Na$_2$SO$_4$ and the solvents drawn off in a vacuum. Chromatography on aluminum oxide (Stage III, neutral) with hexane/acetic ether yields 2.43 g (91%) of the desired compound.

| IR (KBr): | 3520 | cm$^{-1}$ | OH |
| --- | --- | --- | --- |
| | 1615 | } | aromatic substance |
| | 1520 | | |

$^1$H—NMR (TMS as internal standard; CHCl$_3$):
δ (ppm)  0.5 (3H,s,H-18); 0.85 (3H,s,CH$_3$-ketal);
1.02 (3H, s, CH$_3$-ketal); 2.57 (1H,d,J=5 Hz), H-epoxide); 2.92 (1H,d,J=5 Hz, H-epoxide);
2.89 (6H,s,2 × NCH$_3$);
3.4–3.6 (4H,m,OCH$_2$);
4.05–4.25 (1H,m,H-11);
4.37 (1H,s,tert. OH);
6.8 (4H,dd,J$_1$=6 and J$_2$=34 Hz, aromat.-H).

(b)

11β-(4-dimethylaminophenyl)-17α-(methoxymethyl)-3,3-(2,2-dimethylpropane-1,3-dioxy)-9(10)-estrene-5α,17β-diol 1 g (1.97 mmoles) of epoxide are dissolved in 10 ml of abs. methanol and mixed with 20 ml of a 3 m methanolic sodium methanolate solution. After 3 hours of stirring at room temperature the reaction mixture is poured into 150 ml of saturated NH$_4$Cl solution and the aqueous phase extracted with methylene chloride. 1.024 g (96%) of the crude product are obtained when the combined organic phases are washed with water, dried over Na$_2$SO$_4$ and the solvent drawn off in a vacuum.

EXAMPLE 3

11β-(4-dimethylaminophenyl)-17α-(2-methoxyethyl)-17β-hydroxy-4,9(10)-estradien-3-one 632 mg (1.14 mmoles) of 11β-(4-dimethylaminophenyl)-17-(2-methoxyethyl)-3,3-(2,2-dimethylpropane-1,3-dioxy)-9(10)-estrene-5α,17β-diol are converted as described in Example 1. Chromatography on silica gel with hexane/acetic ether yields 285 mg (56%) of the desired final compound.

| IR (KBr): | 3480 | cm$^{-1}$ | OH |
| --- | --- | --- | --- |
| | 1660 | } | unsaturated ketone |
| | 1610 | | |
| | 1515 | | aromatic substance |

$^1$H—NMR (TMS as internal standard; CHCl$_3$):
δ (ppm)  0.59 (3H,s,H-18); 2.9 (6H,s,N(CH$_3$)$_2$);
3.35 (3H,s,OCH$_3$); 3.43 (1H,s,OH);
3.6–3.72 (2H,m,O-CH$_2$);
4.32 (1H,d,J=6,5 Hz,H-11); 5.73 (1H,s,H-4);
6.8 (4H,dd,J$_1$=9 and J$_2$=34 Hz, H-aromat.).

The initial material is prepared in the following way:

(a)

17α-(tert.-butoxycarbonylmethyl)-11β-(4-dimethylaminophenyl)-3,3-(2,2-dimethylpropane-1,3-dioxy)-9(10)-estrene-5α, 17β-diol 4.09 ml (30.38 mmoles) of acetic acid tert.-butylester are dripped at −78° C. into a solution of 31.9 mmoles of lithium-diisopropylamide in 150 ml of abs. tetrahydrofurane. After subsequent stirring for 1 hour the reaction solution is brought to −60° C., and a solution of 3 g (6.08 mmoles) of 11β-(4-dimethylaminophenyl)-3,3-(2,2-dimethylpropane-1,3-dioxy)-5α-hydroxy-9(10)-estren-17-one in 50 ml of abs. tetrahydrofurane is slowly added. After addition the reaction mixture is stirred for one hour before it is mixed with 100 ml of aqueous ammonium-chloride solution. The aqueous phase is extracted with methylene chloride; the residue is chromatographed by way of an aluminum oxide column (neutral, stage III) with hexane/acetic ether after the combined organic phases are dried with sodium sulfate and the solvents drawn off in a vacuum. This yields 2.67 g of the desired product (72%).

(b)

11β-(4-dimethylaminophenyl)-17α-(2-hydroxyethyl)-3,3-(2,2-dimethylpropane-1,3-dioxy)-9(10)-estrene-5α,17β-diol 1.35 g (2.21 mmoles) of the tert. butylester obtained in (a) are dissolved in 30 ml of abs. tetrahydrofurane and mixed with 672 mg (10 eq.) of lithium aluminum hydride. The reaction mixture is subsequently heated to 40° C. for 8 hours and then stirred at room temperature overnight. After addition of 50 ml of methylene chloride the reaction solution is cooled to 0° C. and mixed with a saturated solution of sodium hydrogen carbonate until a flocculent precipitate develops. The excess liquid phase is decanted off, and the precipitate is washed out several times with methylene chloride while being subjected to brisk stirring. After the solvents are drawn off in a vacuum the residue is chromatographed by way of Al$_2$O$_3$ (neutral, stage III) with acetic ether/ethanol. This yields 1.066 g of the desired compound (89%).

(c)

11β-(4-dimethylaminophenyl)-17-(2-methoxyethyl)-3,3-(2,2-dimethylpropane-1,3-dioxy)-9(10)-estrene-5α,17β-diol 1.06 g (1.97 mmoles) of the substance obtained in (b) are dissolved in 50 ml of absolute tetrahydrofurane and mixed with 2.9 ml of a 1.5-molar n-butyl-lithium solution (4.35 mmoles) at 0° C. 0.31 ml (5 mmoles) of methyl iodide are slowly dripped in. After 6 hours of stirring, 25 ml of methanol are added and the reaction mixture concentrated in a vacuum. The organic phase is washed with a saturated solution of NaHCO$_3$ after addition of 100 ml of methylene chloride. The crude product is obtained when the organic phase is dried by way of Na$_2$SO$_4$ and the solvent drawn off in a vacuum. Chromatography on aluminum oxide (neutral, stage III) with acetic ether/hexane yields 632 mg (58%) of the desired ketal.

EXAMPLE 4

11β-(4-dimethylaminophenyl)-17α-ethoxymethyl-17β-hydroxy-4,9(10)-estradien-3-one 665 mg (1.2 mmoles) of 11β-(4-dimethylaminophenyl)-17α-ethoxymethyl-3,3-(2,2-dimethylpropane-1,3-dioxy)-9-estrene-5α,17β-diol are converted as described in Example 1. Chromatography over silica gel with hexane/acetic ether yields 376 mg (80.4%) of the desired final compound. $[\alpha]_D^{25} = 192°$ (c=0.5; CHCl$_3$).

The initial material is prepared in the following way:

760 mg (1.5 mmoles) of the epoxide obtained in Example 2 (a) are dissolved in 50 ml of abs. tetrahydrofurane and mixed with 23 ml of a 2-molar ethanolic ethanolate solution. The solution is then heated to 50° C. for 12 minutes and stirred overnight. The reaction mixture is poured into 50 ml of saturated NH$_4$Cl solution and the aqueous phase extracted with methylene chloride. The combined organic phases are dried over Na$_2$SO$_4$ and the sovent drawn off in a vacuum. This yields 829 mg (99.8%) of the crude product.

EXAMPLE 5

11β-(4-dimethylaminophenyl)-17α-(4-hydroxybut-1(Z)-enyl)-17β-hydroxy-4,9(10)-estradien-3-one The crude product 11β-(4-dimethylaminophenyl)-17β -(4-hydroxybut-1(Z)-enyl)-3,3-(2,2-dimethylpropane-1,3-dioxy)-9(10)-estrene-5α,17β-diol obtained from 500 mg (0.887 mmoles) of hydroxybutinyl adduct (cf. 5 (a)) by hydrogenation converted under the conditions described in Example 1. Chromatography of the residue on silica gel with hexane/acetic ether yields 320 mg (78%) of the title compound.

| IR (KBr): | 3410 | cm$^{-1}$ | OH |
|---|---|---|---|
| | 1655 | } | unsaturated ketone |
| | 1620 | | |
| | 1520 | | aromatic substance |

$^1$H—NMR (TMS as internal standard; CHCl$_3$):
δ (ppm)  0.62 (3H,s,H-18); 2.92 (6H,s,N(CH$_3$)$_2$);
3.5–3.85 (2H,m,O-CH$_2$;
4.28 (1H,d,J=6,5 Hz,H-11);
5.3–5.8 (2H,m,H-olefin.); 5.72 (1H,s,H-4);
6.8 (4H,dd,J$_1$=9 and J$_2$=34 Hz, H-aromat.).

The initial material is obtained in the following way:

(a)

11β-(4-dimethylaminophenyl)-17α-(4-hydroxybut-1-inyl)-3,3-(2,2-dimethylpropane-1,3-dioxy)-9(10)-estrene-5α, 17β-diol 2.962 g (6 mmoles) of 11β-(4-dimethylaminophenyl)-3,3-(2,2-dimethylpropane-1,3-dioxy)-5α-hydroxy-9(10)-estren-17-one are added to 100 ml of abs. tetrahydrofurane at 0° C. and mixed with 7.56 g (90 mmoles) of potassium tert.-butylate. After 3.4 ml (45 mmoles) of 3-butin-1-ol are dripped in, the reaction mixture is slowly heated to 22° C. and stirred for 16 hours at the same temperature. It is then poured into a mixture consisting of 35 ml of 2N HCl and 25 ml of saturated NH$_4$Cl solution and the aqueous phase extracted with methylene chloride. The combined organic phases are dried over Na$_2$SO$_4$ and concentrated until dry in a vacuum. Chromatography of the crude product on Al$_2$O$_3$ (neutral, stage III) with acetic ether/hexane yields 2.43 g (72%) of the desired product.

(b)

11β-(4-dimethylaminophenyl)-17α-(4-hydroxybut-1(Z)-enyl)-3,3-(2,2-dimethylpropane-1,3-dioxy)-9(10)-estrene-5α,17β-diol 500 mg (0.887 mmoles) of the hydroxybutinyl adduct are dissolved in 20 ml of methanol and successively mixed with 1.1 ml of triethylamine and 50 mg of palladium on BaSO$_4$ (10%). Hydrogenation at normal pressure is stopped after one equivalent of hydrogen is taken up. Filtration and concentration of the filtrate until dry yield the desired crude product.

EXAMPLE 6

11β-(4-dimethylaminophenyl)-17α-(2-hydroxyethyl)-17β-hydroxy-4,9(10)-estradien-3-one 1 g of 11β-(4-dimethylaminophenyl)-17α-(2-hydroxyethyl)-3,3-(2,2-dimethylpropane-1,3-dioxy)-9(10)-estrene-5α,17β-diol is split to form the dienone under the conditions described in Example 1. Chromatography of the crude product on silica gel with acetic ether/ethanol yields 610 mg (75%) of the title compound.

| IR (KBr): | 3420 | cm$^{-1}$ | OH |
|---|---|---|---|
| | 1660 | } | unsaturated ketone |
| | 1610 | | |

$^1$H—NMR (TMS as internal standard; CHCl$_3$):
δ (ppm)  0.58 (3H,s,H-18); 2.93 (6H,s,N(CH$_3$)$_2$);
3.75–4.1 (2H,m,O-CH$_2$);
4.35 (1H,d,J=6,5 Hz,H-11); 5.74 (1H,s,H-4);
6.82 (4H,dd,J$_1$=9 and J$_2$=33 Hz, H-aromat.).

The initial material is the compound described in Example 3 (b).

EXAMPLE 7

11β-(4-dimethylaminophenyl)-17α-ethylthiomethyl-17β-hydroxy-4,9(10)-estradien-3-one 774 mg of 11β-(4-dimethylaminophenyl)-17α-ethylthiomethyl-3,3-(2,2-dimethylpropane-1,3-dioxy)-9(10)-estrene-5α,17β-diol are converted under the conditions described in Example 1. Chromatography of the crude product on silica gel with hexane/acetic ether yields 312 mg (47%) of the title compound.
$[\alpha]_D^{25} = 163°$ (c=0.5, CHCl$_3$).

The initial material is obtained in the following way:
1.02 g (2 mmoles) of the epoxide obtained in accordance with Example 2 a) are dissolved in 40 ml of abs. THF and mixed with 2.22 ml of ethane thiol (30 mmoles). After the solution cools to 5° C., 2.24 g (20 mmol) of KOtBu are added and stirred for 14 hours at room temperature. The reaction mixture is then poured into 25 ml of saturated NH$_4$Cl solution and the aqueous phase carefully adjusted to pH 8 with a 1 N HCl solution. 1.13 g of the crude product are obtained, after extraction with methylene chloride, drying of the organic phases over Na$_2$SO$_4$ and removal of the solvent in a vacuum. Chromatography on silica gel with hexane/acetic ether yields 774 mg (68%) of the desired compound.

EXAMPLE 8

11β-(4-dimethylaminophenyl)-17α-(methoxymethyl)-17β-hydroxy-4,9-estradien-3-one-anti-oxime and

EXAMPLE 9

11β-(4-dimethylaminophenyl)-17α-(methoxymethyl)-17β-hydroxy-4,9-estradien-3-one-syn-oxime A solution consisting of 1.5 g of the 11β-(4-dimethylaminophenyl)-17α-(methoxymethyl)-17β-hydroxy-4,9-estradien-3-one obtained in accordance with Example 2 in 20 ml of pyridine is mixed ice-cooled and in portions with 980 mg of hydroylamine hydrochloride. After addition thereof the mixture is stirred for 30 minutes at +5° C., then poured into a mixture of ice water and 0.5 N HCl and extracted with methylene chloride. The crude product is chromatographed on silica gel with hexane/acetic ether, and (a) 820 mg of 11β-(4-dimethylaminophenyl)-17α-(methoxymethyl)-17β-hydroxy-4,9-estradien-3-one-anti-oxime
[UV (MeOH)=288(27400)]

(b) 320 mg of 11β-(4-dimethylaminophenyl)-17α-(methoxymethyl)-17β-hydroxy-4,9-estradien-3-one-syn-oxime
[UV (MeOH)=289(28200)]

are isolated.

EXAMPLE 10

11β-(4-dimethylaminophenyl)-17α-(but-1-in-3-enyl)-17β-hydroxy-4,9-estradien-3-one-anti-oxime and

EXAMPLE 11

11β-(4-dimethylaminophenyl)-17α-(but-1-in-3-enyl)-17β-hydroxy-4,9-estradien-3-one-anti-oxime (a) 905 mg of 11β-(4-dimethylaminophenyl)-17α-(but-1-in-3-enyl)-17β-hydroxy-4,9-estradien-3-one-anti-oxime
[UV (MeOH)=288 (27100)]

(b) 310 mg of 11β-(4-dimethylaminophenyl)-17α-(but-1-in-3-enyl)-17β-hydroxy-4,9-estradien-3-one-syn-oxime
[UV (MeOH)=290 (27500)]

are isolated, in accordance with the instructions for Examples 8 and 9, from 1.5 g of 11β-(4-dimethylaminophenyl)-17α-(but-1-in-3-enyl)-17β-hydroxy-4,9-estradien-3-one (Example 1) after processing and chromatography.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A 11β-aryl-estradiene of the formula wherein
X is hydroxyimino N~OH, where the hydroxy group is in the syn or anti position,
$R^1$ is methyl or ethyl,
$R^2$ is —C≡C—CH=CH$_2$, —CH$_2$—(CH$_2$)$_n$—Y—R$^3$ or —CH=CH—(CH$_2$)$_m$—Y—R$^3$,
Y is oxygen or sulfur,
n is 0 or 1,
m is 1, 2 or 3 and
$R^3$ is hydrogen, $C_{1-4}$-alkyl or $C_{1-4}$-alkanoyl with the proviso that when m is 1 and Y is oxygen, $R^3$ is alkyl of 1 to 4 carbon atoms.

2. A compound of claim 1 wherein $R^2$ is —C≡C—CH=CH$_2$ or —CH=CH—(CH$_2$)$_m$—Y—R$^3$.

3. A compound of claim 1 wherein $R^2$ is —CH$_2$—(CH$_2$)$_n$—Y—R$^3$.

4. A compound of claim 1 wherein Y is S.

5. A compound of claim 1 wherein Y is O.

6. 11β-(4-dimethylaminophenyl)-17α-(ethylthiomethyl)-17β-hydroxy-4,9-estradien-3-one, a compound of claim 1.

7. 11β-(4-dimethylaminophenyl)-17α-(methoxymethyl)-17β-hydroxy-4,9-estradien-3-one-anti-oxime, a compound of claim 1.

8. 11β-(4-dimethylaminophenyl)-17α-(methoxymethyl)17β-hydroxy-4,9-estradien-3-one-syn-oxime, a compound of claim 1.

9. 11β-(4-dimethylaminophenyl)-17α-(but-1-yn-3-enyl)-17β-hydroxy-4,9-estradien-3-one-anti-oxime, a compound of claim 1.

10. 11β-(4-dimethylaminophenyl)-17α-(but-1-yn-3-enyl)-17β-hydroxy-4,9-estradien-3-one-syn-oxime, a compound of claim 1.

11. A pharmaceutical composition comprising an antigestagenic or antiglucocorticoidal efffective amount of a compound of claim 1 and a carrier.

12. A composition of claim 11 wherein the amount of said compound is 10–100 mg.

13. A method of achieving an antigestagenic effect comprising administering a compound of claim 1 to a patient in need of such treatment.

14. A method of achieving an antiglucocorticoidal effect comprising administering a compound of claim 1 to a patient in need of such treatment.

15. A compound of claim 1 wherein $R^2$ is —C≡C—CH=CH$_2$.

16. A compound of claim 1 wherein $R^2$ is —CH$_2$—(CH$_2$)$_n$—Y—R$^3$.

17. A 11β-arly-estradiene of the formula wherein

X is oxygen or hydroxyimino NOH, where the hydroxy group is in the syn or anti position, R¹ is methyl or ethyl, R² is —C≡C—CH=CH₂, —CH₂—(CH₂)$_n$—Y—R³ or —CH=CH—(CH₂)$_m$—Y—R³, Y is sulfur, n is 0 or 1, m is 1, 2 or 3 and R³ is hydrogen, C$_{1-4}$-alkyl or C$_{1-4}$-alkanoyl.

18. A compound of claim 17 wherein X is O.

19. A compound of claim 17 wherein X is NOH.

20. 11β-(4-dimethylaminophenyl)-17α-(but-1-yn-3-enyl)-17β-hydroxy-4,9-estradien-3-one, a compound of claim 17.

21. A compound of claim 17, wherein R² is —C≡C—CH=CH₂ or —CH=CH—(CH₂)$_m$—Y—R³.

22. A compound of claim 17, wherein R² is —CH₂—(CH₂)$_n$—Y—R³.

23. A 11β-aryl-estradiene of the formula wherein

X is oxygen or hydroxyimino NOH, where the hydroxy group is in the syn or anti position, R¹ is methyl or ethyl, R² is —C≡C—CH=CH₂, or —CH₂—(CH₂)$_n$—Y—R³, Y is oxygen or sulfur, n is 0 or 1, m is 1, 2 or 3 and R³ is C$_{1-4}$-alkyl or C$_{1-4}$-alkanoyl, with the proviso that when m is 1 and y is oxygen, R³ is alkyl of 1 to 4 carbon atoms.

24. 11β-(4-dimethylaminophenyl)-17α-(methoxymethyl)-17β-hydroxy-4,9-estradien-3-one, a compound of claim 23.

25. 11β-(4-dimethylaminophenyl)-17α-(2-methoxyethyl)-17β-hydroxy-4,9-estradien-3-one, a compound of claim 23.

26. 11β-(4-dimethylaminophenyl)-17α-(ethoxymethyl)-17β-hydroxy-4,9-estradien-3-one, a compound of claim 23.

27. A compound of claim 23, wherein X is O.

28. A compound of claim 23, wherein X is NOH.

29. A compound of claim 23, wherein Y is S.

30. A compound of claim 23, wherein Y is O.

* * * * *

UNITED STATES PATENT AND TRADEMARK OFFICE
CERTIFICATE OF CORRECTION

PATENT NO. : 4,829,060

DATED : May 9, 1989

INVENTOR(S) : Eckhard Ottow et al

It is certified that error appears in the above-identified patent and that said Letters Patent is hereby corrected as shown below:

Column 14, line 68: reads "17.A 11$\beta$-arly-estradiene of the formula"

should read-- 17.A 11$\beta$-aryl-estradiene of the formula --

Signed and Sealed this

Twenty-fourth Day of October, 1989

*Attest:*

DONALD J. QUIGG

*Attesting Officer*  *Commissioner of Patents and Trademarks*